(12) United States Patent
Klaka et al.

(10) Patent No.: US 11,180,728 B2
(45) Date of Patent: Nov. 23, 2021

(54) IN-VITRO FULL-SKIN MODEL CONTAINING THREE-DIMENSIONAL CELL CULTURE MODELS OF THE SWEAT GLAND

(71) Applicant: Henkel AG & Co. KGaA, Duesseldorf (DE)

(72) Inventors: Patricia Klaka, Leverkusen (DE); Sabine Gruedl, Erkelenz (DE); Melanie Giesen, Geldern (DE); Thomas Welss, Duesseldorf (DE); Bernhard Banowski, Duesseldorf (DE); Lars Vierkotten, Overath (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 448 days.

(21) Appl. No.: 16/095,190

(22) PCT Filed: Mar. 20, 2017

(86) PCT No.: PCT/EP2017/056490
§ 371 (c)(1),
(2) Date: Oct. 19, 2018

(87) PCT Pub. No.: WO2017/182208
PCT Pub. Date: Oct. 26, 2017

(65) Prior Publication Data
US 2019/0144821 A1    May 16, 2019

(30) Foreign Application Priority Data

Apr. 22, 2016   (DE) .................... 10 2016 206 862.8

(51) Int. Cl.
*C12N 5/071* (2010.01)
*G01N 33/50* (2006.01)

(52) U.S. Cl.
CPC .......... *C12N 5/063* (2013.01); *C12N 5/0633* (2013.01); *C12N 5/0698* (2013.01); *G01N 33/5008* (2013.01); *C12N 2513/00* (2013.01); *C12N 2533/54* (2013.01)

(58) Field of Classification Search
CPC .... C12N 5/063; C12N 5/0633; C12N 5/0698; C12N 2533/54
See application file for complete search history.

(56) References Cited

U.S. PATENT DOCUMENTS

2008/0095748 A1* 4/2008 Kharazi .............. A61L 27/3886
                                                         424/93.7

FOREIGN PATENT DOCUMENTS

| CN | 102091352 A | 6/2011 | |
|---|---|---|---|
| DE | 102015222279.9 A1 | 5/2017 | |
| WO | 199615225 A1 | 5/1996 | |
| WO | 2006018147 A2 | 2/2006 | |
| WO | WO-2006018147 A2 * | 2/2006 | ............. A61L 27/60 |
| WO | 2011094963 A1 | 8/2011 | |

OTHER PUBLICATIONS

Huang et al., In vitro constitution and in vivo implantation of engineered skin constructs with sweat glands. Biomaterials, vol. 31, No. 21 (Jul. 2010) pp. 5520-5525. (Year: 2010).*
EPO, International Search Report and Written Opinion issued in International Application No. PCT/EP2017/056490 dated Apr. 27, 2017.
Huang S et al.: "In vitro constitution and 1-10 in vivo implantation of engineered skin constructs with sweat glands", Biomaterials, Elsevier Science Publishers BV., Barking, GB, Bd. 31, Nr. 21, (Apr. 15, 2010), Seiten 5520-5525, XP027059052, ISSN: 0142-9612.
Luca Pontiggia et al: "De Novo Epidermal Regeneration Using Human Eccrine Sweat Gland Cells: Higher Competence of Secretory over Absorptive Cells", Journal of Investigative Dermatology, Bd. 134, Nr. 6, (Feb. 13, 2014), Seiten 1735-1742, XP055367645, US ISSN: 0022-202X.
Huang Sha et al: "3D bioprinted extracellular matrix mimics facilitate directed differentiation of epithelial progenitors for sweat gland regeneration", Acta Biomaterialia, Elsevier, Amsterdam, NL, Bd. 32, 31, (Dec. 31, 2015), Seiten 170-177, XP029415680, ISSN: 1742-7061.
Florian Groeber et al.: "Skin tissue engineering andapplications", Advanced Drug Delivery Reviews, Elsevier, Amsterdam, NL, Bd. 63, Nr. 4, (Jan. 5, 2011), Seiten 352-366, XP028374192, ISSN: 0169-409X.
Li et al: "Matrigel basement membrane matrix induces eccrine sweat gland cells to reconstitute sweat gland-like structures in nude mice"; Experimental Cell Research, 2015, 332, Seiten 67 bis 77.

* cited by examiner

*Primary Examiner* — Kara D Johnson
(74) *Attorney, Agent, or Firm* — Lorenz & Kopf, LLP

(57) ABSTRACT

The present disclosure concerns an in-vitro full skin model which comprises a dermal equivalent and epidermal equivalent as well as from about 1 to about 100 three-dimensional sweat gland equivalents with respectively from about 500 to about 500000 sweat gland cells as well as a diameter of respectively from about 100 to about 6000 μm on a supporting layer. Furthermore, the present disclosure concerns the production of the full skin model as well as the use of this model as an in-vitro model, in screening methods as well as for in-vitro evaluation of the influence of cosmetic substances on the inhibition of sweat secretion as well as body odor.

20 Claims, No Drawings

IN-VITRO FULL-SKIN MODEL CONTAINING THREE-DIMENSIONAL CELL CULTURE MODELS OF THE SWEAT GLAND

CROSS-REFERENCE TO RELATED APPLICATION

This application is a U.S. National-Stage entry under 35 U.S.C. § 371 based on International Application No PCT/EP2017/056490, filed Mar. 20, 2017 which was published under PCT Article 21(2) and which claims priority to German Application No. 10 2016 206 862.8, filed Apr. 22, 2016, which are all hereby incorporated in their entirety by reference.

TECHNICAL FIELD

The present disclosure relates to an in-vitro full skin model with a dermal equivalent and an epidermal equivalent, wherein from about 1 to about 100 three-dimensional sweat gland equivalents with from about 500 to about 500000 sweat gland cells and having a diameter of from about 100 to about 6000 μm are contained in the dermal equivalent and/or epidermal equivalent. By incorporating the sweat gland equivalents into the in-vitro full skin model, the in-vivo situation in the human skin can be effectively emulated. In particular, the in-vivo cell-cell interactions present between the various cell types can be effectively represented, because the three-dimensional sweat gland equivalents also retain their function after incorporation into the full skin model.

The present disclosure furthermore relates to a method for the production of an in-vitro full skin model in which initially, a dermal equivalent is prepared on a supporting layer. Next, an epidermal equivalent is applied to this dermal equivalent. The three-dimensional sweat gland equivalents are introduced into the in-vitro full skin model during the preparation of the dermal equivalent and/or epidermal equivalent.

In addition, the present disclosure relates to the use of an in-vitro full skin model as contemplated herein in cosmetics and in personal hygiene, in particular for the testing, identification and investigation of cosmetic substances, preferably regarding their effectiveness with respect to inhibiting the secretion of sweat and/or body odor as well as for the in-vitro evaluation of the influence of cosmetic substances on the inhibition and/or reduction of sweat secretion and/or body odor.

Finally, the present disclosure relates to a system, in particular a test system, which comprises an in-vitro full skin model as contemplated herein.

BACKGROUND

Washing, cleaning and care of an individual's body is a basic human necessity and modern industry is constantly looking out for ways to meet these human necessities in many ways. What is particularly important for daily hygiene is the persistent removal or at least reduction of body odor and armpit wetness. Armpit wetness and body odor arise through the secretion of eccrine and apocrine sweat glands in the human armpit. While the eccrine glands are responsible for the regulation of heat in the body and are responsible for the occurrence of armpit wetness, the apocrine glands exude a viscous secretion in reaction to stress, and an unpleasant body odor arises when it undergoes bacterial decomposition.

Initial research work on native eccrine and apocrine sweat glands were carried out as early as the beginning of the 20th century in order to classify them into the group of skin appendages belonging to the exocrine gland group. Thereafter, sweat glands were divided into apocrine and eccrine sweat glands as well as a hybrid of apocrine and eccrine sweat glands (also known as apoeccrine sweat glands). The forms mentioned above can be distinguished by their morphological and characteristic features.

The eccrine sweat gland, in particular the human eccrine sweat gland, belongs to the unbranched coiled tubular glands and can be divided into the secretory base (also known as the coil), the dermal excretory duct (also known as the duct) and the epidermal duct (also known as the acrosyringium). The cells present in these sections of the gland have different purposes and functions such as, for example, secretion in the coil, reabsorption of ions in the duct as well as exuding the secretion, in particular sweat, to the surrounding skin through the acrosyringium. The eccrine sweat glands are stimulated by the neurotransmitter acetylcholine (Ach).

In respect of preventing armpit wetness and/or body odor, it is thus desirable to reduce and/or avoid secretions from eccrine and/or apocrine sweat glands. This may be carried out, for example, by obscuring the excretory ducts of eccrine sweat glands by what are known as plugs. In this regard, in the prior art, sweat-inhibiting aluminium and/or aluminium zirconium salts are used; however, these are no longer highly regarded by the consumer. Furthermore, antibacterial agents are used in the prior art which prevent the bacterial decomposition of sweat. However, such agents can have a negative influence on the natural microflora of the skin under the armpit. Thus, it would be a good idea to provide cosmetic agents which are capable of reliably preventing armpit wetness and/or body odor and which contain neither the aluminium and/or aluminium-zirconium salts nor the antibacterial agents used in the prior art. One possibility for preparing such agents arises from using substances which effectively inhibit stimulation of the sweat glands and thus reduce or prevent the secretion of sweat. In order to be able to identify such substances, in-vivo tests with trial participants can be carried out. However, such tests are costly and are not suitable for high-throughput screening methods.

Furthermore, cell models of sweat glands may be used on which the influence of test substances on stimulation of the sweat glands can be investigated. Such models have to simulate the in-vivo situation as closely as possible, and they must be capable of being standardized and must be inexpensive, as well as be suitable for use with high-throughput screening methods. An example of a known three-dimensional sweat gland model from the prior art is described by Li (Li et. al.; "Matrigel basement membrane matrix induces eccrine sweat gland cells to reconstitute sweat gland-like structures in nude mice"; Experimental Cell Research, 2015, 332, pages 67 to 77). In order to produce that sweat gland model, initially, primary sweat gland cells are cultured with growth factors in a gel-like substance (Matrigel®) and then implanted in the backs of live mice. After implantation, spherical structures are formed which express sweat gland-specific marker proteins. Because mice are required to construct the differentiated structures, this model cannot be used in cosmetic and pharmaceutical research, where the use of research animals is prohibited.

Finally, the use of full skin models which also contain sweat glands along with a dermal equivalent and an epidermis, is also known. By punching specimens from native adult human skin, models are obtained which contain all of the skin appendages, which encompasses sweat glands, in this region of the skin. Such models are also known as ex-vivo full skin models. One disadvantage of these models is the low potential for standardization, because it is not possible to control the precise number of sweat glands and in addition, the properties of the model differ from donor to donor.

Thus, there remains a need for in-vitro full skin models which have a similar, preferably identical histological architecture to human skin and which can be produced exclusively using in-vitro methods. It would also be a good idea for these in-vitro full skin models to be capable of standardization and to be produced in an inexpensive manner and be suitable for high-throughput screening methods.

Thus, the objective of the present disclosure is to provide an in-vitro full skin model (hereinbelow also termed a skin equivalent) which has a cell structure and cell-cell interactions which are very similar to the cell structure and cell-cell interactions of native skin and which can be produced exclusively by in-vitro methods. Furthermore, this model should be cheap to produce, be capable of standardization and be suitable for use in high-throughput screening methods.

BRIEF SUMMARY

An in-vitro full skin model is provided herein. The in-vitro full skin model includes, but is not limited to, at least one supporting layer comprising at least one collagen matrix. The in-vitro full skin model further includes, but is not limited to, at least one dermal equivalent. The in-vitro full skin model further includes, but is not limited to, at least one epidermal equivalent. The in-vitro full skin model further includes, but is not limited to, at least one basal membrane. The basal membrane is located between the dermal equivalent and the epidermal equivalent. The dermal equivalent and/or the epidermal equivalent includes from about 1 to about 100 three-dimensional sweat gland equivalent(s), wherein the three-dimensional sweat gland equivalents respectively includes from about 500 to about 500000 sweat gland cells and have a respective diameter of from about 100 to about 6000 μm.

A method for the production of an in-vitro full skin model is also provided herein. The method includes, but is not limited to, the step of providing a suspension of low-solubility collagen. The method further includes, but is not limited to, the step of producing a supporting layer by freeze-drying the collagen suspension. The method further includes, but is not limited to, the step of producing a dermal equivalent by applying primary fibroblasts to the supporting layer and culturing the fibroblasts over a time period of from about 7 to about 28 days. The method further includes, but is not limited to, the step of applying primary keratinocytes to the dermal equivalent and culturing the keratinocytes over a time period of from about 1 to about 10 days. The method further includes, but is not limited to, the step of culturing the model at the air-medium boundary over a time period of from about 7 to about 42 days wherein from about 1 to about 100 three-dimensional sweat gland equivalents with a cell count of respectively from about 500 to about 500000 sweat gland cells and a diameter of respectively from about 100 to about 6000 μm are introduced by adding the dermal equivalents.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now surprisingly been discovered that by introducing three-dimensional sweat gland equivalents into a dermal equivalent and/or epidermal equivalent of a skin equivalent, models can be obtained in which the cell-cell interactions between the various cell types almost correspond to those in native skin. Production is exclusively by employing in-vitro methods and has a high potential for standardization as well as allowing the skin equivalent to be produced inexpensively. In this manner, these skin equivalents are particularly suitable for use in high-throughput screening methods to test sweat-inhibiting substances for use in cosmetics and in pharmaceuticals.

In a first aspect, the present disclosure thus provides an in-vitro full skin model, comprising
a) at least one supporting layer comprising at least one collagen matrix,
b) at least one dermal equivalent,
c) at least one epidermal equivalent,
d) at least one basal membrane, wherein said basal membrane is located between the dermal equivalent and the epidermal equivalent, exemplified in that the dermal equivalent b) and/or the epidermal equivalent c) comprises from about 1 to about 100 three-dimensional sweat gland equivalent(s), wherein the three-dimensional sweat gland equivalents respectively comprise from about 500 to about 500000 sweat gland cells and have a respective diameter of from about 100 to about 6000 μm.

By introducing the three-dimensional sweat gland equivalents into the in-vitro full skin models as contemplated herein, the cell-cell interactions present in human skin are emulated. These models therefore effectively represent the in-vivo situation, so that the results obtained with these models are more relevant than results which are obtained from full skin models without sweat gland equivalents. In addition, the eccrine sweat gland cells contained in the three-dimensional sweat gland equivalents have a potential stem cell activity for wound healing, so that further processes occurring in the skin can be investigated with the skin equivalent as contemplated herein. By using cultured cells for the production of the skin equivalent, a high potential for standardization can be obtained, because a multitude of skin equivalents with the same properties can be produced from the cultured cells. Furthermore, by introducing a precisely determinable number of three-dimensional sweat gland equivalents, a high potential for standardization can be ensured.

The term "in-vitro full skin model" (hereinafter also known as a skin equivalent) should be understood to mean a model of the skin which can be produced exclusively using in-vitro methods and which has both a stratified epidermis and a dermis and wherein a basal membrane is positioned between the dermis and the epidermis.

Furthermore, the term "supporting layer" as used in the context of the present disclosure should be understood to mean a self-supporting layer which acts as a base or scaffold for the dermal equivalent of the skin equivalent as contemplated herein. Preferably, this layer is positioned in the wells of the microtitre plates used for the production of the skin equivalent. In accordance with the present disclosure, this layer comprises a collagen matrix, wherein the term "collagen matrix" should be understood to mean a spatial network formed from collagen, which is preferably provided with pores. However, this does not include a matrix which is formed by the collagen produced by the fibroblasts of the dermis.

In addition, the term "dermal equivalent" as used in the context of the present disclosure means a connective tissue-like layer formed from fibroblasts which substantially correspond to the native dermis.

Furthermore, the term "epidermal equivalent" as used in the context of the present disclosure means a preferably multi-layered layer formed from keratinocytes in the form of a stratified epidermis which substantially corresponds to the native epidermis.

Furthermore, the term "basal membrane" should be understood to mean a layer formed from a preferably multi-layered web formed from collagen, in particular collagen IV, which is intertwined with a two-dimensional network formed from laminin. The cohesion between the collagen web and the laminin network is preferably ensured by perlecan (a proteoglycan formed from heparin sulphate) as well as entactin (also known as nidogen).

Finally, the term "three-dimensional sweat gland equivalent" as used in the present disclosure should be understood to mean a cell model formed from sweat gland cells which extends in all three directions in space and in which the cells have a similar function, in particular an identical function, to cells in a native sweat gland.

The in-vitro full skin model as contemplated herein comprises a supporting layer which contains a collagen matrix as the first essential component a).

In the context of the present disclosure, the skin equivalent preferably comprises a matrix formed from specific collagen compounds as the supporting layer. Thus, as contemplated herein, it is advantageous for the collagen matrix to comprise a low-solubility collagen, in particular a low-solubility collagen formed from horse, pig or cattle tendons. The term "low-solubility collagen" as used in the present disclosure should be understood to mean coarse-fibred collagen which exhibits no visible or only slight swelling in an aqueous medium over at least about 5 hours, or which exhibits no or only slight gel formation. Collagen of this type is preferably obtained from the tendons of animals, in particular mammals, preferably from horses, pigs or cattle, more particularly preferably from the Achilles tendons or skin from cattle, in particular from the Achilles tendons from cattle.

In accordance with the present disclosure, it has been shown to be particularly advantageous for the matrix used as the supporting layer to be formed from freeze-dried low-solubility collagen. Preferred embodiments of the present disclosure are therefore exemplified in that the collagen matrix comprises a freeze-dried low-solubility collagen, in particular a freeze-dried low-solubility collagen formed from tendons from horses, pigs or cattle. The term "freeze-dried low-solubility collagen" as used as contemplated herein should be understood to mean a low-solubility collagen which is obtained by freeze-drying a homogeneous suspension of this low-solubility collagen in a solvent, preferably water. Freeze-drying is also known as sublimation drying and in this instance means drying a deep-frozen material under high vacuum by freezing out the solvent, preferably in the form of water, which then evaporates off in the frozen state. Particularly preferably, this collagen matrix formed from freeze-dried low-solubility collagen has on its surface a skin with pores, These pores lead to a particularly good colonization of the support material with fibroblasts during the construction of the dermal equivalent, so that a disturbance during the differentiation of the fibroblasts, which is necessary for the formation of the dermal equivalent, is avoided.

In the context of the present disclosure, it has been shown to be advantageous for the collagen matrix of the supporting layer to contain a specific total quantity of collagen. Preferred embodiments of the present disclosure are thus exemplified in that the collagen matrix contains a total quantity of collagen, in particular freeze-dried low-solubility collagen, of from about 0.5% to about 5.0% by weight, preferably from about 0.8% to about 3.5% by weight, more preferably from about 0.8% to about 2.5% by weight, in particular from about 0.8% to about 1.2% by weight, with respect to the total weight of the collagen matrix. Supporting layers which contain the total quantities of collagen given above, in particular freeze-dried low-solubility collagen, result in an effective stabilization of the skin equivalent as contemplated herein, and in this manner mean that the equivalents can be readily handled.

The use of cross-linked collagen matrices has been shown to be advantageous in order to prevent the skin equivalent as contemplated herein from contracting. Avoiding contraction constitutes a high potential for standardization, because the test substances can always be applied to an identically sized surface. In this manner, variations in concentration following application of the test substances can be avoided. Thus, as contemplated herein, it is preferable for the collagen matrix to be a cross-linked collagen matrix. Cross-linking of the collagen matrix may, for example, be carried out by employing chemical or physical methods. In the case of chemical cross-linking, chemical cross-linking agents are used in particular; physical cross-linking may, for example, be carried out using UV irradiation or dehydrothermal cross-linking (also known as DHT).

In this connection, it has been shown to be particularly advantageous for the collagen matrix to be cross-linked by employing chemical cross-linking agents. Thus, in the context of the present disclosure, it is preferable for the cross-linking of the collagen matrix to be carried out by employing a chemical cross-linking agent from the group formed by glutaraldehyde, p-benzoquinone, dimethyl adipimidate, dimethyl pimelinidate, dimethyl suberimidate, 1,4-phenylenediisothiocyanate, polyoxyethylene-bis-(imidazolyl carbonyl), bis[polyoxyethylene-bis(imidazolyl carbonyl)] and suberinic acid bis(N-hydroxysuccinimide ester), 1-ethyl-3-(3-dimethylaminopropyl) carbodiimide, enzymes as well as mixtures thereof, in particular glutaraldehyde. The Applicant has surprisingly established that cross-linking of the collagen matrix using the chemical cross-linking agent glutaraldehyde results in excellent stabilization of the skin equivalents without the cytotoxic and apoptotic properties of the glutaraldehyde having a negative influence on the in-vitro full skin model.

The in-vitro full skin model as contemplated herein comprises a dermal equivalent as the second essential component.

This dermal equivalent is preferably formed by dermal fibroblasts. Preferred embodiments of the present disclosure are therefore exemplified in that the dermal equivalent is formed from primary fibroblasts, in particular human primary fibroblasts. The term "primary fibroblasts" should preferably be understood to mean fibroblasts which are naturally present, in particular in the human dermis, genetically modified fibroblasts, fibroblasts from spontaneous mutations or their precursors. Particularly preferably, human primary pre-cultured fibroblasts are used to form the dermal equivalent. Pre-cultured human primary fibroblasts may also be obtained by culturing human primary fibroblasts, wherein the culture is preferably carried out in-vitro by cell proliferation. To pre-culture the fibroblasts, a DMEM medium (Dulbecco's Modified Eagle Medium) is preferably employed.

It has been shown to be advantageous for the dermal equivalent as contemplated herein to contain a specific total cell count of primary fibroblasts. Thus, in the context of the present disclosure, the dermal equivalent preferably contains primary fibroblasts, in particular human primary fibroblasts, in a total cell count of $5 \times 10^5$ to $6 \times 10^6$, preferably $6 \times 10^5$ to $5 \times 10^6$, in particular $7 \times 10^5$ to $4 \times 10^6$. Dermal equivalents which contain said total cell counts of primary fibroblasts exhibit differentiation which is very similar to the differentiation in the dermis of the human skin. This ensures that the in-vitro full skin model as contemplated herein emulates the in-vivo situation as closely as possible.

The in-vitro full skin model as contemplated herein contains at least one epidermal equivalent as the third essential component c).

This epidermal equivalent is preferably formed from primary keratinocytes. The term "keratinocytes" as used in the present disclosure should be understood to mean cells of the epidermis which form a keratinized squamous epithelium, genetically modified keratinocytes, and keratinocytes obtained from spontaneous mutations as well as their precursors. Because the formation of a properly differentiated epidermal equivalent with intact cornification of the basal stem cell fraction depends on the keratinocytes used for the formation of the epidermal equivalent, substantially undifferentiated keratinocyte stem cells from untreated biopsy tissue are preferably used. Preferred embodiments of the present disclosure are therefore exemplified in that the epidermal equivalent is formed from primary keratinocytes, in particular human primary keratinocytes. Preferably, the epidermal equivalent is formed from pre-cultured keratinocytes which are obtained by culturing primary keratinocytes, preferably by proliferation of these cells. In order to carry out the pre-culture of the keratinocytes, a mixture of DMEM medium (Dulbecco's Modified Eagle Medium) and Ham's F12 medium is preferably used.

Particularly preferably, the epidermal equivalent has a plurality of layers of cells which differ from each other. Thus, as contemplated herein, preferably, the epidermal equivalent comprises a plurality of layers of cells which differ from one another, in particular at least two differently differentiated layers of cells as well as at least one keratinized layer of cells. The term "plurality of layers of cells" as used in the present disclosure should be understood to mean at least two layers of cells which differ from each other, in particular from about 2 to about 20 layers of cells which differ from one another. The presence of different layers of cells in the epidermis may be determined with the aid of an optical microscope, for example. Particularly preferably, the epidermal equivalent is provided with from about 2 to about 10 layers of cells which differ from one another, wherein at least one of said layers of cells is selected from the stratum corneum, stratum spinosum and the stratum granulosum.

In accordance with the present disclosure, it has been shown to be advantageous for the epidermal equivalent to contain a specific total cell count of primary keratinocytes. Thus, in the context of the present disclosure, preferably, the epidermal equivalent contains primary keratinocytes, in particular human primary keratinocytes, in a total cell count of from about $4 \times 10^5$ to about $5 \times 10^6$, preferably from about $5.5 \times 10^5$ to about $4 \times 10^6$, in particular from about $6.5 \times 10^5$ to about $3.5 \times 10^6$. Epidermal equivalents which contain the total cell counts of primary keratinocytes defined above exhibit a differentiation which is very similar to the differentiation in the epidermis of human skin. This ensures that the in-vitro full skin model as contemplated herein imitates the in-vivo situation as closely as possible.

The full skin model as contemplated herein comprises a basal membrane which is located between the dermis and the epidermal equivalent as the fourth essential component.

Preferably, in the context of the present disclosure, the basal membrane of the full skin model comprises specific proteins. Preferred embodiments of the present disclosure are therefore exemplified in that the basal membrane comprises proteins from the group formed by laminin, collagen type IV as well as a mixture thereof. Basal membranes which contain the proteins listed above result in a particularly effective bond between the dermis and the epidermal equivalent, and in this manner ensure good stability and handling of the full skin model as contemplated herein.

Preferably, the full skin models as contemplated herein contain from about 1 to about 100 three-dimensional sweat gland equivalents. Incorporation of the three-dimensional sweat gland equivalents means that the in-vivo situation in the human skin is reproduced better than in full skin models which do not contain sweat glands or sweat gland equivalents. The incorporation of an equal number of discrete sweat gland equivalents also means that full skin models can be produced in a more standardized manner than when compared with the use of punched biopsies, which each have a variable number of sweat glands in these biopsies. Preferred embodiments of the present disclosure are thus exemplified in that the dermal equivalent b) and/or the epidermal equivalent c) comprises from about 2 to about 100 three-dimensional sweat gland equivalents, preferably from about 5 to about 100 three-dimensional sweat gland equivalents, more preferably from about 20 to about 100 three-dimensional sweat gland equivalents, in particular from about 50 to about 100 three-dimensional sweat gland equivalents.

The discrete three-dimensional sweat gland equivalents contained in the full skin model as contemplated herein may, for example, be produced by employing the hanging drop method using primary sweat gland cells and using in-vitro methods exclusively. To this end, initially, sweat glands from skin biopsies, in particular native eccrine and/or apocrine sweat glands from skin biopsies are isolated. The isolation may be carried out by employing enzymatic digestion of the human skin using a mixture of from about 2 to about 3 mg/mL of collagenase II and from about 0.1 to about 0.2 mg/n of thermolysin for from about 3 to about 6 hours at from about 35° C. to about 40° C., in particular at about 37° C. Primary sweat gland cells can be obtained by culturing the isolated sweat glands. After careful trypsinization to dissociate the primary sweat gland cells, they are cultured for from about 7 to about 28 days in monolayer cultures and then suspended in a nutrient medium formed by DMEM and Ham's F12 in a weight ratio of about 3:1 which additionally contains about 10% by weight of foetal calf serum (FCS) with respect to the total weight of the mixture. After adjusting the concentration from about 50 to about 250000, in particular from about 400 to about 600 cells per μL of medium, from about 10 to about 100 μL, in particular from about 40 to about 60 μL of this suspension undergoes hanging drop culture in a hanging drop multi-well plate for from about 2 to about 7 days at a temperature of from about 36° C. to about 38° C. and with a $CO_2$ content of about 5% by weight with respect to the total weight of the atmosphere used for culture, whereupon three-dimensional sweat gland equivalents are formed. These equivalents can be integrated into the full skin model immediately following harvest thereof or after further culture for from about 1 to about 6 days. Harvesting may be carried out by adding from about 70 to about 100 μL of the nutrient medium described above. The production of the three-dimensional sweat gland equivalents contained in the full skin model as contemplated herein is described in German patent DE 10 2015 222 279.9, filed on 12 Nov. 2015; its entire disclosure is incorporated herein by reference.

In accordance with the present disclosure and preferably, the three-dimensional sweat gland equivalents are contained in the dermal equivalent. Incorporating these sweat gland equivalents into the dermal equivalent allows for a better imitation of the in-vivo situation. Thus, as contemplated herein, it is advantageous for the dermal equivalent b) to comprise the three-dimensional sweat gland equivalents. By introducing the three-dimensional sweat gland equivalents into the dermal equivalent, cell-cell interactions are enabled which also occur in-vivo and which, for example, are involved in wound healing processes.

Preferably, three-dimensional sweat gland equivalents which have a specific diameter are contained in the full skin model as contemplated herein. Thus, advantageously, as contemplated herein, the three-dimensional sweat gland equivalents respectively have a diameter of from about 100 to about 40000 μm, preferably from about 100 to about 3000 μm, in particular from about 200 to about 2500 μm. The diameter data in this regard refer to the diameter of an individual three-dimensional sweat gland equivalent. The diameter of the spherical sweat gland equivalents as contemplated herein may, for example, be measured by microscopic measurement employing "CellSens" software.

In the context of the present disclosure, the sweat gland equivalents contained in the full skin model as contemplated herein are free from matrix compounds and/or supports. The term "matrix compounds" should be understood here to mean compounds which are capable of forming spatial networks. However, this does not include the substances produced and excreted by the cells themselves which are capable of forming spatial networks. Furthermore, the term "supports" as used in the present disclosure means self-supporting substances which can act as a base or frame for the sweat gland cells. In accordance with a preferred embodiment of the present disclosure, the three-dimensional sweat gland equivalents are respectively free from matrix compounds and/or supports, in particular free from matrix compounds and supports.

The term "free from" as used in the present disclosure should be understood to mean that the three-dimensional sweat gland equivalents contain less than about 1% by weight, with respect to the total weight of the three-dimensional sweat gland equivalent, of matrix compounds and/or supports. Thus, in the context of the present disclosure, advantageously, the three-dimensional sweat gland equivalent contains from about 0 to about 1% by weight, preferably from about 0 to about 0.5% by weight, preferably from about 0 to about 0.2% by weight, in particular about 0% by weight, with respect to the total weight of the three-dimensional sweat gland equivalent, of matrix compounds and supports.

In this connection, it is particularly advantageous for the three-dimensional sweat gland equivalents to be free from specific matrix compounds and supports. Thus, preferably, the three-dimensional sweat gland equivalent does not contain any matrix compounds and/or supports which are selected from the group formed by collagens, in particular collagen type I and/or type III and/or type IV, scleroproteins, gelatines, chitosans, glucosamines, glucosaminoglucans (GAG), heparin sulphate proteoglucans, sulphated glycoproteins, growth factors, cross-linked polysaccharides, cross-linked polypeptides, as well as mixtures thereof.

Particularly preferably, the three-dimensional sweat gland equivalents contained in the skin equivalent as contemplated herein are equivalents of eccrine and/or apocrine human sweat glands. Preferred embodiments of the present disclosure are therefore exemplified in that the three-dimensional sweat gland equivalents are respectively three-dimensional sweat gland equivalents of the eccrine and/or apocrine human sweat gland. Full skin models which contain such sweat gland equivalents are particularly well suited to the identification of sweat-inhibiting substances for in-vivo use in humans.

Particularly preferred full skin models as contemplated herein are described below.

A particularly preferred embodiment of this inventive subject matter is constituted by an in-vitro full skin model comprising:

a) at least one supporting layer comprising at least one collagen matrix, wherein the collagen matrix contains a total quantity of freeze-dried low-solubility collagen of from about 0.8% to about 1.2% by weight with respect to the total weight of the collagen matrix, and wherein the collagen matrix is a cross-linked collagen matrix,
b) at least one dermal equivalent,
c) at least one epidermal equivalent,
d) at least one basal membrane, wherein said basal membrane is located between the dermal equivalent and the epidermal equivalent, exemplified in that the dermal equivalent b) and/or the epidermal equivalent c) comprises from about 1 to about 100 three-dimensional sweat gland equivalent(s), wherein the three-dimensional sweat gland equivalents respectively comprise from about 500 to about 500000 sweat gland cells and have a respective diameter of from about 100 to about 6000 μm.

Furthermore, a particularly preferred embodiment of this inventive subject matter is constituted by an in-vitro full skin model comprising:

a) at least one supporting layer comprising at least one collagen matrix, wherein the collagen matrix contains a total quantity of freeze-dried low-solubility collagen of from about 0.8% to about 1.2% by weight with respect to the total weight of the collagen matrix, and wherein the collagen matrix is a cross-linked collagen matrix,
b) at least one dermal equivalent, wherein the dermal equivalent is formed from human primary fibroblasts,
c) at least one epidermal equivalent,
d) at least one basal membrane, wherein said basal membrane is located between the dermal equivalent and the epidermal equivalent, exemplified in that the dermal equivalent b) and/or the epidermal equivalent c) comprises from about 1 to about 100 three-dimensional sweat gland equivalent(s), wherein the three-dimensional sweat gland equivalents respectively comprise from about 500 to about 500000 sweat gland cells and have a respective diameter of from about 100 to about 6000 μm.

Moreover, a particularly preferred embodiment of this inventive subject matter is constituted by an in-vitro full skin model comprising:
a) at least one supporting layer comprising at least one collagen matrix, wherein the collagen matrix contains a total quantity of freeze-dried low-solubility collagen of from about 0.8% to about 1.2% by weight with respect to the total weight of the collagen matrix, and wherein the collagen matrix is a cross-linked collagen matrix,
b) at least one dermal equivalent, wherein the dermal equivalent is formed from human primary fibroblasts,
c) at least one epidermal equivalent, wherein the epidermal equivalent is formed from human primary keratinocytes and wherein the epidermal equivalent comprises at least two differently differentiated layers of cells as well as at least one keratinized layer of cells,
d) at least one basal membrane, wherein said basal membrane is located between the dermal equivalent and the epidermal equivalent,
exemplified in that
the dermal equivalent b) and/or the epidermal equivalent c) comprises from about 1 to about 100 three-dimensional sweat gland equivalent(s), wherein the three-dimensional sweat gland equivalents respectively comprise from about 500 to about 500000 sweat gland cells and have a respective diameter of from about 100 to about 6000 μm.

In addition, a particularly preferred embodiment of this inventive subject matter is constituted by an in-vitro full skin model comprising:
a) at least one supporting layer comprising at least one collagen matrix, wherein the collagen matrix contains a total quantity of freeze-dried low-solubility collagen of from about 0.8% to about 1.2% by weight with respect to the total weight of the collagen matrix, and wherein the collagen matrix is a cross-linked collagen matrix,
b) at least one dermal equivalent, wherein the dermal equivalent is formed from human primary fibroblasts,
c) at least one epidermal equivalent, wherein the epidermal equivalent is formed from human primary keratinocytes and wherein the epidermal equivalent comprises at least two differently differentiated layers of cells as well as at least one keratinized layer of cells,
d) at least one basal membrane, wherein said basal membrane is located between the dermal equivalent and the epidermal equivalent and wherein the basal membrane comprises proteins from the group formed by laminin, collagen type IV as well as mixtures thereof,
exemplified in that
the dermal equivalent b) and/or the epidermal equivalent c) comprises from about 1 to about 100 three-dimensional sweat gland equivalent(s), wherein the three-dimensional sweat gland equivalents respectively comprise from about 500 to about 500000 sweat gland cells and have a respective diameter of from about 100 to about 6000 μm.

Finally, a particularly preferred embodiment of this inventive subject matter is constituted by an in-vitro full skin model comprising:
a) at least one supporting layer comprising at least one collagen matrix, wherein the collagen matrix contains a total quantity of freeze-dried low-solubility collagen of from about 0.8% to about 1.2% by weight with respect to the total weight of the collagen matrix, and wherein the collagen matrix is a cross-linked collagen matrix,
b) at least one dermal equivalent, wherein the dermal equivalent is formed from human primary fibroblasts,
c) at least one epidermal equivalent, wherein the epidermal equivalent is formed from human primary keratinocytes and wherein the epidermal equivalent comprises at least two differently differentiated layers of cells as well as at least one keratinized layer of cells,
d) at least one basal membrane, wherein said basal membrane is located between the dermal equivalent and the epidermal equivalent and wherein the basal membrane comprises proteins from the group formed by laminin, collagen type IV as well as mixtures thereof,
exemplified in that
the dermal equivalent b) comprises from about 50 to about 100 three-dimensional sweat gland equivalents, wherein the three-dimensional sweat gland equivalents respectively comprise from about 500 to about 500000 sweat gland cells and have a respective diameter of from about 200 to about 2500 μm and wherein the three-dimensional sweat gland equivalents are respectively three-dimensional sweat gland equivalents of eccrine and/or apocrine human sweat glands.

The in-vivo full skin models as contemplated herein have a higher potential for standardizability and availability than the currently used punched biopsies and are closer to the in-vivo situation than full skin models which do not contain any sweat glands and/or sweat gland equivalents. Furthermore, these skin equivalents constitute a cheap alternative to in-vivo studies in humans because, by using this full skin model, the sweat-inhibiting action of test substances can be investigated, for example by comparing gene expression or protein expression upon stimulation with acetylcholine (Ach) in the presence and absence of a specific test substance. The full skin models as contemplated herein simulate the human skin in-vivo both as regards their structure and also their histological composition, so that the information obtained with these models is readily applicable to humans and can also be compared with data for compounds which have already been tested in-vivo.

In a second aspect, the present disclosure provides a method for the production of an in-vitro full skin model, wherein the method comprises the following steps in the specified sequence:
a) providing a suspension of low-solubility collagen,
b) producing the supporting layer by freeze-drying the collagen suspension provided in step a),
c) producing the dermal equivalent by applying primary fibroblasts, in particular human primary fibroblasts, to the supporting layer produced in step b) and culturing said fibroblasts over a time period of from about 7 to about 28 days,
d) applying primary keratinocytes, in particular human primary keratinocytes, to the dermal equivalent produced in step c) and culturing said keratinocytes over a time period of from about 1 to about 10 days,
e) culturing the model obtained after step d) at the air-medium boundary over a time period of from about 7 to about 42 days, rom about
wherein from about 1 to about 100 three-dimensional sweat gland equivalents with a cell count of respectively from about 500 to about 500000 sweat gland cells and a diameter of respectively from about 100 to about 6000 μm are introduced by adding said equivalents in step c) and/or step d).

The term "suspension of low-solubility collagen" as used in the context of the present disclosure should be understood to mean a homogeneous mixture of solid collagen in a solvent, preferably water. In order to produce the homogeneous suspension, equipment such as static mixers or Ultra-Turrax mixers, which are known to the person skilled in the art, may be used.

Furthermore, the term "culturing" preferably means in-vitro maintenance of the life functions of cells, in particular of fibroblasts and keratinocytes, in a suitable environment, for example with the addition and removal of metabolic educts and products, and in particular the proliferation of cells.

In the context of the method as contemplated herein, it has been shown to be advantageous for the suspension provided in method step a) to contain a specific total quantity of collagen. Preferred embodiments of the method as contemplated herein are thus exemplified in that the suspension of low-solubility collagen in step a) contains a total quantity of collagen of from about 0.2% to about 4.0% by weight, preferably from about 0.3% to about 3.0% by weight, more preferably from about 0.4% to about 2.0% by weight, in particular from about 0.5% to about 1.5% by weight with respect to the total weight of the suspension. Using suspensions with the aforementioned total quantities of collagen means that particularly stable supporting layers are formed, so that high stability and good handleability of the full skin models resulting from the method as contemplated herein are guaranteed.

Furthermore, in the context of the method as contemplated herein, it has been shown to be advantageous for the suspension of low-solubility collagen in step a) to have a pH of about 0.1 to a pH of about 6.9, preferably a pH of about 2.0 to a pH of about 5.0, more preferably a pH of about 3.0 to a pH of about 4.5, in particular a pH of about 3.5 to a pH of about 4.0. Using suspensions with the aforementioned pH values means that particularly stable supporting layers are formed.

Prior to freeze-drying in method step b), the collagen suspension is preferably placed in containers with dimensions that correspond to the desired supporting layer. In the context of the method, suitable containers are, for example, the wells of microtitre plates. In addition, it is possible to coat these containers with suitable agents prior to adding the collagen suspension, in order to improve adhesion of the supporting layer to the vessel wall. Examples of suitable agents are gelatin, polylysine, fibrin or fibrinogen/thrombin or fibronectin. In this regard, firstly, the internal vessel walls are wetted with the aforementioned agents and then dried, so that a layer of the agents remains adhered to the internal vessel surface. Next, the collagen suspension is added. The freeze-drying carried out in method step b) is preferably carried out in these vessels. Furthermore, as contemplated herein, the freeze-drying is preferably carried out at a specific cooling rate. Thus, in the context of the present disclosure, preferably, the freeze-drying of the collagen suspension in step b) is carried out at a cooling rate of from about 5° C. to about 40° C. per hour, preferably from about 10° C. to about 30° C. per hour, more preferably from about 18° C. to about 23° C. per hour, in particular from about 20° C. to about 22° C. per hour. The slow cooling rate results in the formation of a thin skin at the surface of the freeze-dried supporting layer, wherein the thin skin has pores on the surface. These pores constitute particularly good conditions for subsequent colonization with fibroblasts, because they promote slow migration of the fibroblasts into the supporting layer. Higher cooling rates than those mentioned above, on the other hand, will result in a supporting layer with larger pores which the fibroblasts cannot completely fill with newly synthesized extra cellular matrix in the given culturing time. Seeded fibroblasts can then aggregate in these large pores and differentiate, whereupon the layering and thereby the differentiation of the dermis can be substantially perturbed. The cooling rate mentioned above thus ensures that a supporting layer is provided which can be optimally colonized by the fibroblasts. In this manner, unperturbed differentiation can be achieved which also corresponds to that in human skin.

If a cross-linked collagen matrix is to be used as the supporting substance, cross-linking of this matrix is carried out after the freeze-drying described in method step c). In this regard, the cross-linking agents described above in connection with the first aspect of the present disclosure may be used. Particularly preferably, glutaraldehyde is used for cross-linking. The cross-linking means that a contraction process in the full skin model during production is avoided so that high reproducibility can be guaranteed because of the uniform size and capabilities.

Obtaining and culturing the fibroblasts used for the production of the dermal equivalent is carried out using methods which are known to the person skilled in the art. Preferably, fibroblasts from a suitable pass, in particular the third or fourth pass, are pre-cultured in a cell culture flask and are dissociated from the base by trypsinization immediately prior to use. The nutrient medium for culturing the fibroblasts may, for example, be DMEM, which contains about 10% by weight of FCS.

In accordance with the present disclosure, it has been shown to be advantageous for the production of the dermal equivalent to use specified total concentrations of fibroblasts. Preferred embodiments of the present disclosure are therefore exemplified in that for the production of the dermal equivalent in step c), primary fibroblasts, in particular human primary fibroblasts, are used in a total concentration of from about $2\times10^5$ to about $2\times10^6$ cells per mL of medium, preferably from about $3\times10^5$ to about $1\times10^6$ cells per mL of medium, more preferably from about $4\times10^5$ to about $7\times10^5$ cells per mL of medium, in particular from about $4.5\times10^5$ to about $5.5\times10^5$ cells per mL of medium. The medium is preferably a DMEM medium which contains about 10% by weight of FCS. For the purposes of further stabilization, additional human fibronectin and/or laminin may be added to the culture medium. The term "fibronectin" means structural or adhesion proteins produced in fibroblasts which function in-vivo to bind other macromolecules, for example collagen, and which are involved in the adhesion of cells to neighbouring cells. Laminin is a protein of the basal membrane to which cells can adhere. Adding fibronectin and/or laminin to the culture medium mutually reinforce binding of the fibroblasts to the supporting layer. Employing the aforementioned total concentrations ensures sufficient colonization of the supporting layer with the fibroblasts. The cell count of the primary fibroblasts may, for example, be determined using a conventional counting chamber as well as trypan blue. To this end, a trypan blue solution is added to an undiluted suspension of cultured primary fibroblasts and the number of cells in the appropriate corner squares is determined. The arithmetic mean is produced from these values. Considering the volume of the counting chamber, the dilution factor and the feed factor, a cell count per mL or L is determined from this mean value. The cell count used in method step c) in this regard is in respect of the number of live cells (live count).

Culture of the fibroblasts applied to the supporting layer in method step c) is preferably carried out in a submersion culture. This should be understood to mean culturing of fibroblasts covered with nutrient solution. A barrier function may additionally be produced by changing the culturing conditions or by adding chemical substances such as ceramides and vitamin to the medium. Preferably, as contemplated herein, the culture of the primary fibroblasts in particular the human primary fibroblasts in step c) is carried out over a time period of from about 8 to about 25 days, preferably from about 10 to about 22 days, preferably from about 11 to about 20 days, in particular from about 12 to about 18 days, at a temperature of from about 30° C. to about 40° C.

Obtaining and culture of the keratinocytes used to produce the epidermal equivalent is carried out using methods which are known to the person skilled in the art. Preferably, keratinocytes from a suitable pass, in particular the third or fourth pass, are pre-cultured in a cell culture flask and are dissociated from the base by trypsinization immediately prior to use. The nutrient medium for culturing the fibroblasts may, for example, be DMEM and Ham's F12 medium which contains from about 1% to about 30% by weight of FCS as well as other serum products and additives.

In method step d), keratinocytes are applied to the dermal equivalent produced in method step c). Here again, it has been shown to be advantageous for the keratinocytes to be used in a specific total concentration. Thus, as contemplated herein, it is advantageous for the primary keratinocytes, in particular human primary keratinocytes, to be used in step d) in a total concentration of from about $1.5 \times 10^5$ to about $1 \times 10^6$ cells per mL of medium, preferably from about from about $2.5 \times 10^5$ to about $9 \times 10^5$ cells per mL of medium, more preferably from about $3.5 \times 10^5$ to about $7 \times 10^5$ cells per mL of medium, in particular $4 \times 10^5$ to about $5 \times 10^5$ cells per mL of medium. Using the aforementioned total concentrations guarantees sufficient colonization of the dermal equivalent with the keratinocytes. The cell count may be determined in the manner described above in connection with the cell count for the fibroblasts.

The keratinocytes applied in method step d) are preferably cultured for a specific period in a submersion culture. Thus, in the context of the present disclosure, it is preferable for the primary keratinocytes, in particular the human primary keratinocytes, to be cultured in step d) under submersion culture over a time period of from about 1 to about 8 days, preferably from about 1 to about 6 days, more preferably from about 1 to about 4 days, in particular from about 1 to about 2 days, at a temperature of from about 30° C. to about 40° C. Particularly preferably, the keratinocytes are seeded onto the supporting layer in a cell culture medium, particularly preferably DMEM/F12 medium, which contains approximately from about 1% to about 30% by weight, with respect to the total weight of the medium, of foetal calf serum (FCS), NCS, defined serum or serum replacement products and various additives which promote the proliferation and differentiation of the cells. Next, the supporting layer is covered with DMEM medium in particular containing mouse EGF or comparable preparations from other animals, epidermal growth factor (hEGF) (for example in a concentration of about 0.2 μg/L of medium) and, for example, about 0.8 mM of $CaCl_2$), and then undergo submersion culture, preferably for from about 1 to about 8 days.

Complete differentiation of the keratinocyte layers is achieved by culture of the keratinocytes at the medium-air boundary. This type of culture is also known as airlift culture, wherein DMEM without hEGF and BPE (bovine pituitary extract) is used as the culture medium. The term "airlift culture" should be understood to mean a culture in which the height of the nutrient medium surface is set at exactly the height of the dermal equivalent, while the layers of cells formed by the keratinocytes lie above the surface of the nutrient medium and are not covered by the nutrient medium, i.e. culture is carried out at the air-nutrient medium boundary layer, whereupon the cultures are supplied from below. Subsequently, the models are lifted from the wells in the microtitre plate and placed on filter papers which rest on metallic spacers in petri dishes. The medium is poured into the petri dishes to a depth such that it does not completely cover the filter paper, but rather, it forms a collar of liquid around the base of the skin model (also known as an air-liquid interface). During culture at the air-nutrient medium boundary, an epidermal equivalent which is typical of skin is formed. Particularly preferred embodiments of the method as contemplated herein are thus exemplified in that the culturing of the model obtained after step d) at the air-medium boundary is carried out over a time period of from about 8 to about 35 days, preferably from about 9 to about 30 days, more preferably from about 10 to about 20 days, in particular from about 10 to about 13 days, at a temperature of from about 30° C. to about 40° C.

The three-dimensional sweat gland equivalents in the method as contemplated herein are introduced in method step c) and/or d). Introduction of the sweat gland equivalents in method step c) during the production of the dermal equivalent is preferred as contemplated herein, because in this manner, the in-vivo situation can be closely emulated. Thus, as contemplated herein, it is preferable for the three-dimensional sweat gland equivalents to be introduced in step c), wherein the primary fibroblasts, in particular the human primary fibroblasts, are mixed with the three-dimensional sweat gland equivalents and then are applied to the supporting layer produced in step b).

However, as contemplated herein, it is also possible to introduce the three-dimensional sweat gland equivalents during step d) of the method as contemplated herein. Thus, it is also preferable as contemplated herein for the three-dimensional sweat gland equivalents to be introduced in step d), wherein the three-dimensional sweat gland equivalents are seeded from about 1 to about 3 hours before applying the primary keratinocytes, in particular human primary keratinocytes. The term "seeding" should be understood herein to mean applying the three-dimensional sweat gland equivalents onto the surface of the dermal equivalent.

In accordance with the present disclosure, from about 1 to about 100 discrete sweat gland equivalents each with a cell count of from about 500 to about 500000 cells as well as a diameter of from about 100 to about 6000 μm are introduced in the method steps c) and/or d). In the context of the present disclosure, however, it has been shown to be advantageous for a larger number of sweat gland equivalents with a smaller diameter to be introduced into the full skin model. Thus, in the context of the present disclosure, preferably, from about 50 to about 100 three-dimensional sweat gland equivalents with a cell count of respectively from about 500 to about 500000 sweat gland cells and a diameter of respectively from about 500 to about 2500 μm may be introduced in step c) and/or in step d), in particular in step c).

Particularly preferred methods as contemplated herein will now be described for the production of in-vitro full skin models. These methods preferably concern methods in which all of the method steps are exclusively carried out using in-vitro methods.

Thus, a particularly preferred embodiment of this subject matter of the present disclosure is constituted by a method for the production of an in-vitro full skin model, wherein the method comprises the following steps in the specified sequence:
a) providing a suspension of low-solubility collagen, wherein the suspension of low-solubility collagen in step a) contains a total quantity of collagen of from about 0.2% to about 4.0% by weight, preferably from about 0.3% to about 3.0% by weight, more preferably from about 0.4% to about 2.0% by weight, in particular from about 0.5% to about 1.5% by weight with respect to the total weight of the suspension, and wherein the suspension of low-solubility collagen in step a) has a pH of about 0.1 to a pH of about 6.9, preferably a pH of about 2.0 to a pH of about 5.0, more preferably a pH of about 3.0 to a pH of about 4.5, in particular a pH of about 3.5 to a pH of about 4.0, b) producing the supporting layer by freeze-drying the collagen suspension provided in step a), c) producing the dermal equivalent by applying primary fibroblasts, in particular human primary fibroblasts, to the supporting layer produced in step b) and culturing said fibroblasts over a time period of from about 7 to about 28 days, d) applying primary keratinocytes, in particular human primary keratinocytes, to the dermal equivalent produced in step c) and culturing said keratinocytes over a time period of from about 1 to about 10 days, e) culturing the model obtained after step d) at the air-medium boundary over a time period of from about 7 to about 42 days, wherein from about 1 to about 100 three-dimensional sweat gland equivalents with a cell count of respectively from about 500 to about 500000 sweat gland cells and a diameter of respectively from about 100 to about 6000 µm are introduced by adding said equivalents in step c) and/or step d).

A further particularly preferred embodiment of this subject matter of the present disclosure is accordingly constituted by a method for the production of an in-vitro full skin model, wherein the method comprises the following steps in the specified sequence:

a) providing a suspension of low-solubility collagen, wherein the suspension of low-solubility collagen in step a) contains a total quantity of collagen of from about 0.2% to about 4.0% by weight, preferably from about 0.3% to about 3.0% by weight, more preferably from about 0.4% to about 2.0% by weight, in particular from about 0.5% to about 1.5% by weight with respect to the total weight of the suspension, and wherein the suspension of low-solubility collagen in step a) has a pH of about 0.1 to a pH of about 6.9, preferably a pH of about 2.0 to a pH of about 5.0, more preferably a pH of about 3.0 to a pH of about 4.5, in particular a pH of about 3.5 to a pH of about 4.0, b) producing the supporting layer by freeze-drying the collagen suspension provided in step a), wherein the freeze-drying of the collagen suspension in step b) is carried out at a cooling rate of from about 5° C. to about 40° C. per hour, preferably from about 10° C. to about 30° C. per hour, more preferably from about 18° C. to about 23° C. per hour, in particular from about 20° C. to about 22° C. per hour, c) producing the dermal equivalent by applying primary fibroblasts, in particular human primary fibroblasts, to the supporting layer produced in step b) and culturing said fibroblasts over a time period of from about 7 to about 28 days wherein, in order to produce the dermal equivalent in step c), primary fibroblasts, in particular human primary fibroblasts, are used in a total concentration of from about $2\times10^5$ to about $2\times10^6$ cells per mL of medium, preferably from about $3\times10^5$ to about $1\times10^6$ cells per mL of medium, more preferably from about $4\times10^5$ to about $7\times10^5$ cells per mL of medium, in particular from about $4.5\times10^5$ to about $5.5\times10^5$ cells per mL of medium, d) applying primary keratinocytes, in particular human primary keratinocytes, to the dermal equivalent produced in step c) and culturing said keratinocytes over a time period of from about 1 to about 10 days, e) culturing the model obtained after step d) at the air-medium boundary over a time period of from about 7 to about 42 days, wherein from about 1 to about 100 three-dimensional sweat gland equivalents with a cell count of respectively from about 500 to about 500000 sweat gland cells and a diameter of respectively from about 100 to about 6000 µm are introduced by adding said equivalents in step c) and/or step d).

A yet still further particularly preferred embodiment of this subject matter of the present disclosure is accordingly constituted by a method for the production of an in-vitro full skin model, wherein the method comprises the following steps in the specified sequence:

a) providing a suspension of low-solubility collagen, wherein the suspension of low-solubility collagen in step a) contains a total quantity of collagen of from about 0.2% to about 4.0% by weight, preferably from about 0.3% to about 3.0% by weight, more preferably from about 0.4% to about 2.0% by weight, in particular from about 0.5% to about 1.5% by weight with respect to the total weight of the suspension, and wherein the suspension of low-solubility collagen in step a) has a pH of about 0.1 to a pH of about 6.9, preferably a pH of about 2.0 to a pH of about 5.0, more preferably a pH of about 3.0 to a pH of about 4.5, in particular a pH of about 3.5 to a pH of about 4.0, b) producing the supporting layer by freeze-drying the collagen suspension provided in step a), wherein the freeze-drying of the collagen suspension in step b) is carried out at a cooling rate of from about 5° C. to about 40° C. per hour, preferably from about 10° C. to about 30° C. per hour, more preferably from about 18° C. to about 23° C. per hour, in particular from about 20° C. to about 22° C. per hour, c) producing the dermal equivalent by applying primary fibroblasts, in particular human primary fibroblasts, to the supporting layer produced in step b) and culturing said fibroblasts over a time period of from about 7 to about 28 days wherein, in order to produce the dermal equivalent in step c), primary fibroblasts, in particular human primary fibroblasts, are used in a total concentration of from about $2 \times 10^5$ to about $2 \times 10^6$ cells per mL of medium, preferably from about $3 \times 10^5$ to about $1 \times 10^6$ cells per mL of medium, more preferably from about $4 \times 10^5$ to about $7 \times 10^5$ cells per mL of medium, in particular from about $4.5 \times 10^5$ to about $5.5 \times 10^5$ cells per mL of medium, d) applying primary keratinocytes, in particular human primary keratinocytes, to the dermal equivalent produced in step c) and culturing said keratinocytes over a time period of from about 1 to about 10 days, wherein in step d), primary keratinocytes, in particular human primary keratinocytes, are used in a total concentration of from about $1.5 \times 10^5$ to about $1 \times 10^6$ cells per mL of medium, preferably from about $2.5 \times 10^5$ to about $9 \times 10^5$ cells per mL of medium, more preferably from about $3.5 \times 10^5$ to about $7 \times 10^5$ cells per mL of medium, in particular from about $4 \times 10^5$ to about $5 \times 10^5$ cells per mL of medium, e) culturing the model obtained after step d) at the air-medium boundary over a time period of from about 7 to about 42 days, wherein from about 1 to about 100 three-dimensional sweat gland equivalents with a cell count of respectively from about 500 to about 500000 sweat gland cells and a diameter of respectively from about 100 to about 6000 μm are introduced by adding said equivalents in step c) and/or step d).

Finally, a yet still further particularly preferred embodiment of this subject matter of the present disclosure is accordingly constituted by a method for the production of an in-vitro full skin model, wherein the method comprises the following steps in the specified sequence:

a) providing a suspension of low-solubility collagen, wherein the suspension of low-solubility collagen in step a) contains a total quantity of collagen of from about 0.2% to about 4.0% by weight, preferably from about 0.3% to about 3.0% by weight, more preferably from about 0.4% to about 2.0% by weight, in particular from about 0.5% to about 1.5% by weight with respect to the total weight of the suspension, and wherein the suspension of low-solubility collagen in step a) has a pH of about 0.1 to a pH of about 6.9, preferably a pH of about 2.0 to a pH of about 5.0, more preferably a pH of about 3.0 to a pH of about 4.5, in particular a pH of about 3.5 to a pH of about 4.0, b) producing the supporting layer by freeze-drying the collagen suspension provided in step a), wherein the freeze-drying of the collagen suspension in step b) is carried out at a cooling rate of from about 5° C. to about 40° C. per hour, preferably from about 10° C. to about 30° C. per hour, more preferably from about 18° C. to about 23° C. per hour, in particular from about 20° C. to about 22° C. per hour, c) producing the dermal equivalent by applying primary fibroblasts, in particular human primary fibroblasts, to the supporting layer produced in step b) and culturing said fibroblasts over a time period of from about 7 to about 28 days wherein, in order to produce the dermal equivalent in step c), primary fibroblasts, in particular human primary fibroblasts, are used in a total concentration of from about $2 \times 10^5$ to about $2 \times 10^6$ cells per mL of medium, preferably from about $3 \times 10^5$ to about $1 \times 10^6$ cells per mL of medium, more preferably from about $4 \times 10^5$ to about $7 \times 10^5$ cells per mL of medium, in particular from about $4.5 \times 10^5$ to about $5.5 \times 10^5$ cells per mL of medium, d) applying primary keratinocytes, in particular human primary keratinocytes, to the dermal equivalent produced in step c) and culturing said keratinocytes over a time period of from about 1 to about 10 days, wherein in step d), primary keratinocytes, in particular human primary keratinocytes, are used in a total concentration of from about $1.5 \times 10^5$ to about $1 \times 10^6$ cells per mL of medium, preferably from about $2.5 \times 10^5$ to about $9 \times 10^5$ cells per mL of medium, more preferably from about $3.5 \times 10^5$ to about $7 \times 10^5$ cells per mL of medium, in particular from about $4 \times 10^5$ to about $5 \times 10^5$ cells per mL of medium, e) culturing the model obtained after step d) at the air-medium boundary over a time period of from about 7 to about 42 days, wherein from about 50 to about 100 three-dimensional sweat gland equivalents with a cell count of respectively from about 500 to about 500000 sweat gland cells and a diameter of respectively from about 100 to about 6000 μm are introduced by adding these equivalents in step c).

Three-dimensional sweat gland equivalents of the eccrine and/or apocrine human sweat gland are preferably introduced in the method described above for the production of in-vitro full skin models.

The methods as contemplated herein have the advantage that, in order to produce the in-vitro full skin model, it is not necessary to make use of any in-vivo methods. As a consequence, these models may also be used to test substances which are envisaged for cosmetic use. Furthermore, the method as contemplated herein provides for the inexpensive production of standardized models which can be used in screening methods with high-throughput rates. In addition, this production method results in full skin models which have differently differentiated layers of cells and express sweat gland-specific markers so that the in-vitro data generated with these models can be made to be applicable to the in-vivo situation.

The statements regarding the in-vitro full skin models as contemplated herein apply mutatis mutandis to further preferred embodiments of the method as contemplated herein.

In a third aspect, the present disclosure concerns the use of the in-vitro full skin model as contemplated herein in cosmetics and in personal hygiene, in particular for the testing, identification and investigation of cosmetic substances, preferably as regards their effectiveness in respect of the inhibition and/or reduction of body sweat and/or body odor. As already mentioned, this full skin model may be used as an in-vitro model for the determination of the influence of test substances on sweat glands in the field of cosmetics and in particular that of personal hygiene. Because of the high potential for standardization that is possible as well as good simulation of the in-vivo situation, the full skin models as contemplated herein may in particular be used to discover novel sweat-inhibiting substances. The full skin model as contemplated herein is particularly suitable for product testing, for example in regard to effectiveness, undesirable side effects, for example irritation, toxicity and inflammation effects, allergy-triggering effects or the tolerance to substances. Furthermore, the full skin model as contemplated herein may also be used for studies regarding resorption, transport and/or penetration of substances, as well as for wound healing. Furthermore, with this model, the effects of external environmental influences, such as irradiation, heat, radioactivity, electrical fields or the like, on the skin can be investigated. The action of such influences may, for example, be determined by evaluating the gene expression, metabolism, proliferation, differentiation as well as cell reorganization. It is also possible for the in-vitro full skin model as contemplated herein to be colonized with microorganisms, in particular pathogenic microorganisms such as fungi, bacteria and viruses, in order to study infection processes and healing.

Statements regarding the in-vitro full skin models and the method as contemplated herein apply mutatis mutandis to the further preferred embodiments of the use as contemplated herein.

In a further aspect, the present disclosure concerns the use of an in-vitro full skin model as contemplated herein in preferably automated screening methods, in particular for the testing, identification and investigation of cosmetic substances, preferably as regards their effectiveness in respect of the inhibition and/or reduction of body sweat and/or body odor.

Statements regarding the in-vitro full skin models and the method as contemplated herein apply mutatis mutandis to the further preferred embodiments of the use as contemplated herein.

In a further aspect, the present disclosure concerns the use of an in-vitro full skin model as contemplated herein for the in-vitro evaluation of the influence of cosmetic substances on the inhibition and/or reduction of sweat secretions and/or body odor.

Statements regarding the three-dimensional sweat gland equivalents and the method as contemplated herein apply mutatis mutandis to the further preferred embodiments of the use as contemplated herein.

Finally, in a further aspect, the present disclosure concerns a system, in particular a test system, comprising an in-vitro full skin model as contemplated herein.

Statements regarding the three-dimensional sweat gland equivalents and the method as contemplated herein apply mutatis mutandis to the further preferred embodiments of the use as contemplated herein.

In summary, the present disclosure is in particular exemplified by the following points:

In-vitro full skin model, comprising
a) at least one supporting layer comprising at least one collagen matrix,
b) at least one dermal equivalent,
c) at least one epidermal equivalent,
d) at least one basal membrane, wherein said basal membrane is located between the dermal equivalent and the epidermal equivalent,
exemplified in that
the dermal equivalent b) and/or the epidermal equivalent c) comprises from about 1 to about 100 three-dimensional sweat gland equivalent(s), wherein the three-dimensional sweat gland equivalents respectively comprise from about 500 to about 500000 sweat gland cells and have a respective diameter of from about 100 to about 6000 µm.

In-vitro full skin model according to point 1, exemplified in that the collagen matrix comprises a low-solubility collagen, in particular a low-solubility collagen formed from tendons from horses, pigs or cattle.

In-vitro full skin model according to one of points 1 or 2, exemplified in that the collagen matrix comprises a freeze-dried low-solubility collagen, in particular a low-solubility collagen formed from tendons from horses, pigs or cattle.

In-vitro full skin model according to one of the preceding points, exemplified in that the collagen matrix contains a total quantity of collagen, in particular freeze-dried low-solubility collagen, of from about 0.5% to about 5.0% by weight, preferably from about 0.8% to about 3.5% by weight, more preferably from about 0.8% to about 2.5% by weight, in particular from about 0.8% to about 1.2% by weight, with respect to the total weight of the collagen matrix.

In-vitro full skin model according to one of the preceding points, exemplified in that the collagen matrix is a cross-linked collagen matrix.

In-vitro full skin model according to point 5, exemplified in that the cross-linking of the collagen matrix is carried out by employing a chemical cross-linking agent from the group formed by glutaraldehyde, p-benzoquinone, dimethyl adipimidate, dimethyl pimelinidate, dimethyl suberimidate, 1,4-phenylendiisothiocyanate, polyoxyethylene-bis-(imidazolyl carbonyl), bis[polyoxyethylene-bis(imidazolyl carbonyl)] and suberinic acid bis(N-hydroxysuccinimide ester), 1-ethyl-3-(3-dimethyl aminopropyl)-carbodiimide, enzymes as well as mixtures thereof, in particular glutaraldehyde.

In-vitro full skin model according to one of the preceding points, exemplified in that the dermal equivalent is formed from primary fibroblasts, in particular human primary fibroblasts.

In-vitro full skin model according to one of the preceding points, exemplified in that the dermal equivalent contains primary fibroblasts, in particular human primary fibroblasts, in a total cell count of from about $5 \times 10^5$ to about $6 \times 10^6$, preferably from about $6 \times 10^5$ to about $5 \times 10^6$, in particular from about $7 \times 10^5$ to about $4 \times 10^6$.

In-vitro full skin model according to one of the preceding points, exemplified in that the epidermal equivalent is formed from primary keratinocytes, in particular human primary keratinocytes.

In-vitro full skin model according to one of the preceding points, exemplified in that the epidermal equivalent comprises a plurality of mutually different layers of cells, in particular at least two mutually different layers of cells as well as at least one keratinized layer of cells.

In-vitro full skin model according to one of the preceding points, exemplified in that the epidermal equivalent contains primary keratinocytes, in particular human primary keratinocytes, in a total cell count of from about $4 \times 10^5$ to about $5 \times 10^6$, preferably from about $5.5 \times 10^5$ to about $4 \times 10^6$, in particular from about $6.5 \times 10^5$ to about $3.5 \times 10^6$.

In-vitro full skin model according to one of the preceding points, exemplified in that the basal membrane comprises proteins from the group formed by laminin, collagen type IV as well as mixtures thereof.

In-vitro full skin model according to one of the preceding points, exemplified in that the dermal equivalent b) and/or the epidermal equivalent c) comprises from about 2 to about 100 three-dimensional sweat gland equivalents, preferably from about 5 to about 100 three-dimensional sweat gland equivalents, more preferably from about 20 to about 100 three-dimensional sweat gland equivalents, in particular from about 50 to about 100 three-dimensional sweat gland equivalents.

In-vitro full skin model according to one of the preceding points, exemplified in that the dermal equivalent b) comprises the three-dimensional sweat gland equivalents.

In-vitro full skin model according to one of the preceding points, exemplified in that the three-dimensional sweat gland equivalents respectively have a diameter of from about 100 to about 4000 μm, preferably from about 100 to about 3000 μm, in particular from about 200 to about 2500 μm.

In-vitro full skin model according to one of the preceding points, exemplified in that the three-dimensional sweat gland equivalents are respectively free from matrix compounds and/or supports, in particular free from matrix compounds and supports.

In-vitro full skin model according to point 16, exemplified in that the matrix compounds and/or supports are selected from the group formed by collagens, in particular collagen type I and/or type III and/or type IV, scleroproteins, gelatines, chitosans, glucosamines, glucosaminoglucans (GAG), heparin sulphate proteoglucans, sulphated glycoproteins, growth factors, cross-linked polysaccharides, cross-linked polypeptides as well as mixtures thereof.

In-vitro full skin model according to one of the preceding points, exemplified in that the three-dimensional sweat gland equivalents are respectively three-dimensional sweat gland equivalents of the eccrine and/or apocrine human sweat gland.

A method for the production of an in-vitro full skin model, wherein the method comprises the following steps in the specified sequence:
a) providing a suspension of low-solubility collagen,
b) producing the supporting layer by freeze-drying the collagen suspension provided in step a),
c) producing the dermal equivalent by applying primary fibroblasts, in particular human primary fibroblasts, to the supporting layer produced in step b) and culturing said fibroblasts over a time period of from about 7 to about 28 days,
d) applying primary keratinocytes, in particular human primary keratinocytes, to the dermal equivalent produced in step c) and culturing said keratinocytes over a time period of from about 1 to about 10 days,
e) culturing the model obtained after step d) at the air-medium boundary over a time period of from about 7 to about 42 days,
   wherein from about 1 to about 100 three-dimensional sweat gland equivalents with a cell count of respectively from about 500 to about 500000 sweat gland cells and a diameter of respectively from about 100 to about 6000 μm are introduced by adding said equivalents in step c) and/or step d).

Method according to point 19, exemplified in that the suspension of low-solubility collagen in step a) contains a total quantity of collagen of from about 0.2% to about 4.0% by weight, preferably from about 0.3% to about 3.0% by weight, more preferably from about 0.4% to about 2.0% by weight, in particular from about 0.5% to about 1.5% by weight, with respect to the total weight of the suspension.

Method according to one of points 19 or 20, exemplified in that the suspension of low-solubility collagen in step a) has a pH of about 0.1 to a pH of about 6.9, preferably a pH of about 2.0 to a pH of about 5.0, more preferably a pH of about 3.0 to a pH of about 4.5, in particular a pH of about 3.5 to a pH of about 4.0.

Method according to one of points 19 to 21, exemplified in that the freeze-drying of the collagen suspension in step b) is carried out at a cooling rate of from about 5° C. to about 40° C. per hour, preferably from about 10° C. to about 30° C. per hour, more preferably from about 18° C. to about 23° C. per hour, in particular from about 20° C. to about 22° C. per hour.

Method according to one of points 19 to 22, exemplified in that in order to produce the dermal equivalents in step c), primary fibroblasts, in particular human primary fibroblasts, are used in a total concentration of from about $2 \times 10^5$ to about $2 \times 10^6$ cells per mL of medium, preferably from about $3 \times 10^5$ to about $1 \times 10^6$ cells per mL of medium, more preferably from about $4 \times 10^5$ to about $7 \times 10^5$ cells per mL of medium, in particular from about $4.5 \times 10^5$ to about $5.5 \times 10^5$ cells per mL of medium.

Method according to one of points 19 to 23, exemplified in that culture of the primary fibroblasts, in particular the human primary fibroblasts, is carried out in step c) over a time period of from about 8 to about 25 days, preferably from about 10 to about 22 days, more preferably from about 11 to about 20 days, in particular from about 12 to about 18 days, at a temperature of from about 30° C. to about 40° C.

Method according to one of points 19 to 24, exemplified in that in step d), primary keratinocytes, in particular human primary keratinocytes, are used in a total concentration of from about $1.5 \times 10^5$ to about $1 \times 10^6$ cells per mL of medium, preferably from about $2.5 \times 10^5$ to about $9 \times 10^5$ cells per mL of medium, more preferably from about $3.5 \times 10^5$ to about $7 \times 10^5$ cells per mL of medium, in particular from about $4 \times 10^5$ to about $5 \times 10^5$ cells per mL of medium.

Method according to one of points 19 to 25, exemplified in that culture of the primary keratinocytes, in particular the human primary keratinocytes, is carried out in step d) in a submersion culture over a time period of from about 1 to about 8 days, preferably from about 1 to about 6 days, more preferably from about 1 to about 4 days, in particular from about 1 to about 2 days, at a temperature of from about 30° C. to about 40° C.

Method according to one of points 19 to 26, exemplified in that culture of the model obtained after step d) is carried out at the air-medium boundary over a time period of from about 8 to about 35 days, preferably from about 9 to about 30 days, more preferably from about 10 to about 20 days, in particular from about 10 to about 13 days, at a temperature of from about 30° C. to about 40° C.

Method according to one of points 19 to 27, exemplified in that the three-dimensional sweat gland equivalents are introduced in step c), wherein the primary fibroblasts, in particular the human primary fibroblasts, are mixed with the three-dimensional sweat gland equivalents and then applied to the supporting layer produced in step b).

Method according to one of points 19 to 27, exemplified in that the three-dimensional sweat gland equivalents are introduced in step d), wherein the three-dimensional sweat gland equivalents are seeded from about 1 to about 3 hours before applying the primary keratinocytes, in particular human primary keratinocytes.

Method according to one of points 19 to 29, exemplified in that from about 50 to about 100 three-dimensional sweat gland equivalents with a cell count of respectively from about 50 to about 500000 sweat gland cells and a diameter of respectively from about 500 to about 2500 µm are introduced in step c) and/or in step d), in particular in step c).

Use of the in-vitro full skin model according to one of points 1 to 18 in cosmetics and in personal hygiene, in particular for the testing, identification and investigation of cosmetic substances, preferably as regards their effectiveness in respect of the inhibition and/or reduction of body sweat and/or body odor.

Use of an in-vitro full skin model according to one of points 1 to 18 in preferably automated screening methods, in particular for the testing, identification and investigation of cosmetic substances, preferably as regards their effectiveness in respect of inhibiting and/or reducing body sweat and/or body odor.

Use of an in-vitro full skin model according to one of points 1 to 18 for the in-vitro evaluation of the influence of cosmetic substances on the inhibition and/or reduction of sweat secretion and/or body odor.

A system, in particular a test system, comprising an in-vitro full skin model according to one of points 1 to 18.

The following examples illustrate the present disclosure without limiting it in any way.

EXAMPLES

Isolation of Sweat Glands

The native sweat glands were obtained from human tissue samples, what are known as biopsies, taken from patients undergoing plastic surgery and who had agreed that the material could be used for research purposes. The tissue used was removed during upper arm lifts and facelifts. The eccrine and apocrine sweat glands from the armpit region were isolated from these.

To this end, the respective biopsy was divided into small pieces and thereafter cut into pieces with a maximum size of approximately 1 cm×1 cm. Next, the skin was digested with a mixture of equal parts of collagenase 11 (5 mg/mL) and thermolysin (0.25 mg/mL) at 37° C. in an incubator for approximately 3.5 to 5 hours until the connective tissue had been almost completely digested. This mixture was then centrifuged at 1200 rpm for 5 minutes and the supernatant was discarded in order to remove the enzyme solution as well as any surplus fat. The pellet which remained was taken up in DMEM solution and the solution was transferred into a petri dish. Intact sweat glands were isolated under a binocular microscope using a microcapillary and transferred into fresh DMEM medium.

Culturing of Isolated Native Sweat Glands

The sweat glands isolated in step 1.1 were placed in culture flasks coated with collagen I and then 25 mL of nutrient medium was added. After culturing for 7 to 21 days in an incubator at 37° C. and under 5% $CO_2$, the grown sweat gland cells were dissociated and cultured again to confluence (monolayer culture of primary sweat gland cells) in culture flasks coated with collagen I.

The composition of the nutrient medium used was as follows:

| Components of medium | |
|---|---|
| DMEM/Ham's F12 Nutrient Mix | 3:1 |
| Foetal Calf Serum (FCS) | 10% |
| EGF | 10 ng/mL |
| Hydrocortisone | 0.4 µg/mL |
| Insulin | 0.12 UI/mL |

-continued

| Components of medium | |
|---|---|
| Choleratoxin | $10^{-10}$ M |
| Adenine | 2.43 g/mL |
| Gentamicin | 25 µg/mL |
| Penicillin G | 100 UI/mL |
| Triiodothyronine | $2*10^{-9}$ M |
| Ascorbyl-2-phosphate | 1 mM |

Production of the Cell Preparation and the Three-Dimensional Sweat Gland Equivalents After determining the exact cell counts of the above monolayer cultures of the primary sweat gland cells, they were adjusted to a cell count of 10 to 5000 cells per µL using the above nutrient medium, and then 50 µL of this cell suspension was transferred using the "SureDrop® Inlet" system into each well of a "GravityPLUS®" plate (both from Insphero AG, Switzerland). Culturing was carried out at 36° C. to 38° C. and under a $CO_2$ content of 5% by weight with respect to the total weight of the atmosphere used for culture. After 1 to 3 days, respectively 40% by weight of the medium in the wells of the "GravityPLUS®" plate was replaced with fresh nutrient medium. After 3 to 5 days of culture, the 3D sweat gland equivalents were harvested by adding 50 to 200 µL of nutrient medium and transferred into a "GravityTRAP®"-Platte (Insphero AG, Switzerland). Prior to harvesting, the "GravityTRAP®"-Platte was moistened with 60 to 100 µL of keratinocyte medium with the aid of a multi-channel pipette in order to minimize the formation of air bubbles and to prevent loss of the three-dimensional sweat gland equivalents. After harvesting, the plate was centrifuged for 1 to 5 minutes at 100 to 300×g in order to remove air bubbles.

Production of an In-Vitro Full Skin Model with Three-Dimensional Sweat Gland Equivalents in the Dermal Equivalent The production of the supporting layer, which comprised a cross-linked collagen matrix, was carried out in the manner described in Examples 1 and 2 on pages 22 and 23 of the published patent document WO 2006/019147 A1. After sucking off the medium, the supporting layer in the microtitre plates was supplemented with 1 mL of a mixture of pre-cultured fibroblasts ($6\times10^5$ fibroblasts per mL of medium; the medium used was DMEM with 10% by weight FCS, 100 U/mL penicillin G, 25 µg/mL of gentamicin as well as 1 mM of ascorbyl-2-phosphate) with 60 to 100 of the three-dimensional sweat gland equivalents produced as described in point 1.3 (cell count per equivalent approximately 25000 sweat gland cells). To this end, third or fourth pass fibroblasts which had been pre-cultured in culture flasks were dissociated from the bottom of the culture flasks by adding a trypsin solution, washed with medium and centrifuged. After determining the cell count, the cell suspension was adjusted to the concentration given above and the above number of discrete sweat gland equivalents was added. After applying the mixture of fibroblasts and sweat gland equivalents to the supporting layer, the plate lid was closed and the plates were submersion incubated for 16 days at 37° C. and under 5% v/v $CO_2$, wherein the medium was changed every 3 days. After 16 days, a dermal equivalent had been formed into which the three-dimensional sweat gland equivalents had been incorporated. Next, keratinocytes were seeded onto this dermal equivalent. To this end, the first or second pass keratinocytes were pre-cultured in cell culture flasks with the nutrient medium set out in point 1.2 and then dissociated from the bottom by adding a trypsin solution. After washing with nutrient medium and centrifuging, the cell count of the keratinocyte suspension was adjusted to $1-6 \times 10^5$ keratinocytes per mL of medium. The medium was sucked from the wells of the microtitre plate which contained the dermal equivalent until the surface of the dermal equivalent was just moistened. Next, 1 mL of the keratinocyte suspension prepared earlier was added and the plate lid was closed. Culture in submersion culture was carried out for 2 days at 37° C. and under 5% v/v $CO_2$. At the end of the two days, the skin models were removed from the wells and placed on filter papers which were placed on metallic spacers in a petri dish. The petri dish was then filled with the nutrient medium set out in point 1.2 to an extent such that the medium reached the upper edge of the filter paper and distributed itself around the base of the skin models. The surface of the models, on the other hand, was not covered by the medium (airlift culture). After a further 11 days of culture in airlift culture, the in-vitro full skin models as contemplated herein were obtained, which had a multi-layered epidermis as well as a keratinized tissue surface.

Production of an In-Vitro Full Skin Model with Three-Dimensional Sweat Gland Equivalents in the Epidermal Equivalent The supporting layer which supported a dermal equivalent was produced in the manner described in Examples 1 to 3 of published patent document WO 2006/018147 A1 on pages 22 to 24, wherein culture of the fibroblasts was carried out for 16 days. The three-dimensional sweat gland equivalents produced as described in point 1.3 were placed on this dermal equivalent by suspending them in the nutrient medium described in point 1.2 and then applying this suspension to the dermal equivalent. After 1 to 2 hours, the keratinocytes were seeded as described in point 1.4. After 1 day under submersion conditions, the models were transferred into the air-liquid interface culture format and were cultured for a further 11 days under these conditions. The in-vitro full skin models produced in this manner comprised a multi-layered epidermis as well as a keratinized tissue surface.

Analysis of the In-Vitro Full Skin Model

In order to assay protein expression from sweat gland-specific marker proteins, immunofluorescence staining was carried out on histological sections. To this end, the in-vitro full skin models produced as described in points 1.4 and 1.5 were cut into 1×0.5 cm sized pieces and embedded in paraffin or frozen with embedding medium. Next, the objects were sectioned in accordance with a standard fluorescence protocol for histological sections (for example from the manufacturer Abcam, Cambridge, UK) and then stained. The stained samples could then be analysed under a fluorescence microscope or a confocal laser scanning microscope. The following sweat gland-specific marker proteins were assayed: carcinoembryonal antigen (CEA), alpha smooth muscle actin (alpha-SMA), muscarinic acetylcholine receptor M3 (M-ACh-R3), sodium-potassium chloride cotransporter 1 (NKCC1), galanin receptor 2 (GalR2). The expression of sweat gland-specific marker proteins in the in-vitro full skin models as contemplated herein shows that the three-dimensional sweat gland equivalents in this model had retained their natural function. Thus, these models can be used to investigate the influence of substances on sweat inhibition.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. An in-vitro full skin model, comprising
   a) at least one supporting layer comprising at least one collagen matrix,
   b) at least one dermal equivalent,
   c) at least one epidermal equivalent, and
   d) at least one basal membrane, wherein the basal membrane is located between the dermal equivalent and the epidermal equivalent,
   wherein the dermal equivalent b) and/or the epidermal equivalent c) comprises from about 1 to about 100 three-dimensional sweat gland equivalent(s), wherein the three-dimensional sweat gland equivalents respectively comprise from about 500 to about 500000 sweat gland cells and have a respective diameter of from about 100 to about 6000 µm,
   wherein the three-dimensional sweat gland equivalents are free from matrix compounds and supports, and
   wherein the three-dimensional sweat gland equivalents are three-dimensional sweat gland equivalents of the eccrine and/or apocrine human sweat gland.

2. The in-vitro full skin model as claimed in claim 1, wherein:
   the dermal equivalent comprises primary fibroblasts in a total cell count of from about $7 \times 10^5$;
   the dermal equivalent comprises from about 50 to about 100 three-dimensional sweat gland equivalents;
   the collagen matrix comprises a freeze-dried low-solubility collagen formed from tendons from horses, pigs or cattle;
   the collagen matrix contains a total quantity of collagen of from about 0.8% to about 1.2% by weight, with respect to the total weight of the collagen matrix;
   the epidermal equivalent comprises a plurality of layers of cells which differ from one another as well as at least one keratinized layer of cells;
   at least one of the layers of cells is selected from the stratum corneum, stratum spinosum and the stratum granulosum; and
   the basal membrane comprises proteins from the group formed by laminin, collagen type IV as well as a mixture thereof.

3. The in-vitro full skin model as claimed in claim 1, wherein the epidermal equivalent comprises a plurality of layers of cells which differ from one another as well as at least one keratinized layer of cells, wherein at least one of the layers of cells is selected from the stratum corneum, stratum spinosum and the stratum granulosum.

4. The in-vitro full skin model as claimed in claim 1, wherein the epidermal equivalent c) comprises from about 50 to about 100 three-dimensional sweat gland equivalents.

5. The in-vitro full skin model as claimed in claim 1, wherein the three-dimensional sweat gland equivalents are three-dimensional sweat gland equivalents of the apocrine human sweat gland.

6. The in-vitro full skin model as claimed in claim 1, wherein the collagen matrix comprises a freeze-dried low-solubility collagen formed from tendons from horses, pigs or cattle, and wherein the collagen matrix contains a total quantity of collagen, of from about 0.5% to about 5.0% by weight, with respect to the total weight of the collagen matrix.

7. The in-vitro full skin model as claimed in claim 1, wherein the collagen matrix comprises a freeze-dried low-solubility collagen formed from tendons from horses, pigs or cattle, and wherein the collagen matrix contains a total quantity of collagen, of from about 0.8% to about 1.2% by weight, with respect to the total weight of the collagen matrix.

8. The in-vitro full skin model as claimed in claim 7, wherein the collagen matrix is a cross-linked collagen matrix and wherein the cross-linking of the collagen matrix is carried out by employing a chemical cross-linking agent from the group of glutaraldehyde, p-benzoquinone, dimethyl adipimidate, dimethyl pimelinidate, dimethyl suberimidate, 1,4-phenylendiisothiocyanate, polyoxyethylene-bis-(imidazolyl carbonyl), bis[polyoxyethylene-bis(imidazolyl carbonyl)] and suberinic acid bis(N-hydroxysuccinimide ester), 1-ethyl-3-(3-dimethyl aminopropyl)-carbodiimide, and combinations thereof.

9. The in-vitro full skin model as claimed in claim 1, wherein:
the dermal equivalent comprises primary fibroblasts in a total cell count of from about $7\times10^5$ to about $4\times10^6$; and
the dermal equivalent b) and/or the epidermal equivalent c) comprises from about 50 to about 100 three-dimensional sweat gland equivalents.

10. The in-vitro full skin model as claimed in claim 1, wherein the three-dimensional sweat gland equivalents are three-dimensional sweat gland equivalents of the eccrine human sweat gland.

11. A method for the production of an in-vitro full skin model, wherein the method comprises the following steps in the specified sequence:
a) providing a suspension of low-solubility collagen,
b) producing a supporting layer by freeze-drying the collagen suspension provided in step a),
c) producing a dermal equivalent by applying primary fibroblasts to the supporting layer produced in step b) and culturing the fibroblasts over a time period of from about 7 to about 28 days,
d) applying primary keratinocytes to the dermal equivalent produced in step c) and culturing the keratinocytes over a time period of from about 1 to about 10 days,
e) culturing the model obtained after step d) at the air-medium boundary over a time period of from about 7 to about 42 days,
wherein from about 1 to about 100 three-dimensional sweat gland equivalents with a cell count of respectively from about 500 to about 500000 sweat gland cells and a diameter of respectively from about 100 to about 6000 µm are introduced by adding the equivalents in step c) and/or step d);
wherein the three-dimensional sweat gland equivalents are free from matrix compounds and supports; and
wherein the three-dimensional sweat gland equivalents are three-dimensional sweat gland equivalents of the eccrine and/or apocrine human sweat gland.

12. The method as claimed in claim 11, wherein the suspension of low-solubility collagen in step a) contains a total quantity of collagen of from about 0.2% to about 4.0% by weight, with respect to the total weight of the suspension.

13. The method as claimed in claim 11, wherein the suspension of low-solubility collagen in step a) contains a total quantity of collagen of from about 0.5% to about 1.5% by weight, with respect to the total weight of the suspension.

14. The method as claimed in claim 11, wherein the three-dimensional sweat gland equivalents are introduced in step c), wherein the primary fibroblasts are mixed with the three-dimensional sweat gland equivalents and then applied to the supporting layer produced in step b).

15. The in-vitro full skin model as claimed in claim 11, wherein the dermal equivalent comprises from about 50 to about 100 three-dimensional sweat gland equivalents.

16. The method as claimed in claim 11, wherein, in order to produce the dermal equivalents in step c), primary fibroblasts are used in a total concentration of from about $4.5\times10^5$ to about $5.5\times10^5$ cells per mL of medium.

17. The method as claimed in claim 11, wherein in step d), primary keratinocytes are used in a total concentration of from about $4\times10^5$ to about $5\times10^5$ cells per mL of medium.

18. The method as claimed in claim 11, wherein the three-dimensional sweat gland equivalents are three-dimensional sweat gland equivalents of the eccrine human sweat gland.

19. The method as claimed in claim 11, wherein:
the suspension of low-solubility collagen in step a) contains a total quantity of collagen of from about 0.5% to about 1.5% by weight, with respect to the total weight of the suspension; and
the three-dimensional sweat gland equivalents are introduced in step c), wherein the primary fibroblasts are mixed with the three-dimensional sweat gland equivalents and then applied to the supporting layer produced in step b).

20. The method as claimed in claim 19, wherein:
in order to produce the dermal equivalents in step c), primary fibroblasts are used in a total concentration of from about $4.5\times10^5$ to about $5.5\times10^5$ cells per mL of medium;
the dermal equivalent comprises from about 50 to about 100 three-dimensional sweat gland equivalents;
the epidermal equivalent comprises a plurality of layers of cells which differ from one another as well as at least one keratinized layer of cells;
at least one of the layers of cells is selected from the stratum corneum, stratum spinosum and the stratum granulosum; and
the basal membrane comprises proteins from the group formed by laminin, collagen type IV as well as a mixture thereof.

* * * * *